US00PP25226P2

(12) United States Plant Patent
Isobe

(10) Patent No.: US PP25,226 P2
(45) Date of Patent: Jan. 13, 2015

(54) ***ASARINA* PLANT NAMED 'SUNLOROSE'**

(50) Latin Name: ***Asarina* hybrid**
Varietal Denomination: Sunlorose

(71) Applicant: Yasuko Isobe, Shiga (JP)

(72) Inventor: Yasuko Isobe, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 140 days.

(21) Appl. No.: 13/815,128

(22) Filed: Jan. 31, 2013

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

*Primary Examiner* — Annette Para
(74) *Attorney, Agent, or Firm* — C. A. Whealy

(57) ABSTRACT

A new and distinct cultivar of *Asarina* plant named 'Sunlorose', characterized by its trailing plant habit; vigorous growth habit; freely branching habit; freely flowering habit; long flowering period; relatively small vivid red purple-colored flowers; and good garden performance.

1 Drawing Sheet

Botanical designation: *Asarina* hybrid.
Cultivar denomination: 'SUNLOROSE'.

CROSS REFERENCE TO CLOSELY-RELATED APPLICATIONS

Title: Asarina Plant Named 'Sunloshiro'
Applicant: Yasuko Isobe
U.S. Plant patent application Ser. No. 13/815,126

BACKGROUND OF THE INVENTION

The present invention relates to a new and distinct cultivar of *Asarina* plant, botanically known as *Asarina* hybrid and hereinafter referred to by the name 'Sunlorose'.

The new *Asarina* plant is a product of a planned breeding program conducted by the Inventor in Higashiomi, Shiga, Japan. The objective of the breeding program is to create new trailing and freely branching *Asarina* plants with attractive leaf and flower coloration.

The new *Asarina* plant originated from a cross-pollination made by the Inventor in June, 2009 in Higashiomi, Shiga, Japan of a proprietary selection of *Asarina* hybrid identified as code number LP133-1, not patented, as the female, or seed, parent with a proprietary selection of *Asarina* hybrid identified as code number LP115-1, not patented, as the male, or pollen, parent. The new *Asarina* plant was discovered and selected by the Inventor as a single flowering plant within the progeny of the stated cross-pollination in a controlled greenhouse environment in Higashiomi, Shiga, Japan in November, 2010.

Asexual reproduction of the new *Asarina* plant by vegetative cuttings in a controlled environment in Higashiomi, Shiga, Japan since November, 2010 has shown that the unique features of this new *Asarina* plant are stable and reproduced true to type in successive generations.

SUMMARY OF THE INVENTION

Plants of the new *Asarina* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunlorose'. These characteristics in combination distinguish 'Sunlorose' as a new and distinct *Asarina* plant:

1. Trailing plant habit.
2. Vigorous growth habit.
3. Freely branching habit.
4. Freely flowering habit.
5. Long flowering period.
6. Relatively small vivid red purple-colored flowers.
7. Good garden performance.

Plants of the new *Asarina* can be compared to plants of the female parent selection. Plants of the new *Asarina* differ primarily from plants of the female parent selection in the following characteristics:

1. Plants of the new *Asarina* are more freely branching than plants of the female parent selection.
2. Plants of the new *Asarina* have smaller flowers than plants of the female parent selection.
3. Plants of the new *Asarina* and the female parent selection differ in flower color as plants of the female parent selection have white-colored flowers.

Plants of the new *Asarina* can be compared to plants of the male parent selection. Plants of the new *Asarina* differ slightly from plants of the male parent selection in flower color.

Plants of the new *Asarina* can be compared to plants of *Asarina* hybrid 'Sunloshiro', disclosed in a U.S. Plant patent application Ser. No. 13/815,126. Plants of the new *Asarina* differ primarily from plants of 'Sunloshiro' in flower color as plants of 'Sunloshiro' have white-colored flowers.

Plants of the new *Asarina* can also be compared to plants of *Asarina lophospermum*×*A. erubescens* 'Sun-Asaro', disclosed in U.S. Plant Pat. No. 15,532. In side-by-side comparisons conducted in Higashiomi, Shiga, Japan, plants of the new *Asarina* and 'Sun-Asaro' differed primarily in the following characteristics:

1. Plants of the new *Asarina* were more compact than plants of 'Sun-Asaro'.
2. Plants of the new *Asarina* had smaller and darker green-colored leaves than plants of 'Sun-Asaro'.
3. Plants of the new *Asarina* had smaller flowers than plants of 'Sun-Asaro'.
4. Flower petals of plants of the new *Asarina* and 'Sun-Asaro' differed in shape as plants of 'Sun-Asaro' had petals with cuspidate and mucronate apices.
5. Plants of the new *Asarina* and 'Sun-Asaro' differed slightly in flower color.
6. Plants of the new *Asarina* had longer and thicker peduncles than plants of 'Sun-Asaro'.

BRIEF DESCRIPTION OF THE PHOTOGRAPHS

The accompanying colored photographs illustrate the overall appearance of the new *Asarina* plant showing the colors as true as it is reasonably possible to obtain in colored reproductions of this type. Colors in the photographs may differ slightly from the color values cited in the detailed botanical description which accurately describe the colors of the new *Asarina* plant.

The photograph at the top of the sheet comprises a side perspective view of a typical flowering plant of 'Sunlorose' grown in a hanging basket container.

The photograph at the bottom of the sheet is a close-up view of a typical flowering plant of 'Sunlorose'.

DETAILED BOTANICAL DESCRIPTION

The aforementioned photographs and following observations, measurements and values describe plants grown during the summer in 18-cm hanging basket containers in an outdoor nursery Higashiomi, Shiga, Japan and under cultural practices typical of commercial production. During the production of the plants, day temperatures averaged 23° C. and night temperatures averaged 13° C. Plants were four months old when the description was taken and five months old when the photographs were taken. In the following description, color references are made to The Royal Horticultural Society Colour Chart, 2007 Edition, except where general terms of ordinary dictionary significance are used.

Botanical classification: *Asarina hybrid* 'Sunlorose'.

Parentage:

*Female, or seed, parent*.—Proprietary selection of *Asarina* hybrid identified as code number LP133-1, not patented.

*Male, or pollen, parent*.—Proprietary selection of *Asarina* hybrid identified as code number LP115-1, not patented.

Propagation:

*Type*.—By vegetative cuttings.

*Time to initiate roots, summer*.—About ten days at temperatures of 20° C. to 25° C.

*Time to initiate roots, winter*.—About two weeks at temperatures of 15° C. to 20° C.

*Time to produce a rooted young plant, summer*.—About three weeks at temperatures of 20° C. to 25° C.

*Time to produce a rooted young plant, winter*.—About four weeks at temperatures of 15° C. to 20° C.

*Root description*.—Fibrous; white in color.

*Rooting habit*.—Freely branching.

Plant description:

*Plant and growth habit*.—Trailing plant habit; freely branching with lateral branches potentially developing at every node; vigorous growth habit.

*Plant height* (*from soil level*).—About 11.8 cm.

*Plant diameter* (*or spread*).—About 92.4 cm.

Lateral branch description:

*Length*.—About 81 cm.

*Diameter*.—About 1.6 mm.

*Internode length*.—About 3.3 cm.

*Aspect*.—Decumbent.

*Texture*.—Densely pubescent.

*Color*.—Close to 143C.

Foliage description:

*Arrangement*.—Opposite or alternate, simple.

*Length*.—About 5.5 cm.

*Width*.—About 5.6 cm.

*Shape*.—Roughly deltoid.

*Apex*.—Acute.

*Base*.—Cordate.

*Margin*.—Dentate.

*Texture, upper and lower surfaces*.—Pubescent.

*Venation pattern*.—Palmate.

*Color*.—Developing leaves, upper surface: Close to 137C. Developing leaves, lower surface: Close to 137D. Fully expanded leaves, upper surface: Close to 137B; venation, close to 145A. Fully expanded leaves, lower surface: Close to 137D; venation, close to 145B.

*Petiole*.—Length: About 2.5 cm. Diameter: About 1.5 mm. Texture, upper and lower surfaces: Pubescent. Color, upper and lower surfaces: Close to 144B.

Flower description:

*Flower arrangement and flowering habit*.—Single bilabiate flowers arising from upper leaf axils; freely flowering habit with numerous flowers developing per plant; flowers face mostly outwardly.

*Fragrance*.—None detected.

*Natural flowering season*.—Early flowering habit, plants of the new *Asarina* initiate and develop flowers about three months after planting; long flowering period, flowering commences naturally in May and plants flower continuously until October in Japan.

*Flower longevity*.—Individual flowers last about one week on the plant; flowers not persistent.

*Flower buds*.—Length: About 4 cm. Diameter: About 7.8 mm. Shape: Elongated globose. Color: Close to 144B; apex, close to 70B.

*Flower diameter*.—About 3.2 cm.

*Flower length* (*depth*).—About 5.5 cm.

*Throat diameter*.—About 1.3 cm.

*Tube diameter, mid-section*.—About 8.3 mm.

*Tube diameter, base*.—About 4.5 mm.

*Tube length*.—About 4.4 cm.

*Corolla*.—Arrangement: Bilabiate with a two-lobed upper lip and three-lobed lower lip. Length, upper lip: About 1.3 cm. Length, lower lip: About 1.3 cm to 1.4 cm. Width, upper lip: About 1.7 cm. Width, lower lip: About 1.3 cm to 1.5 cm. Shape, upper lip: Two-lobed, imbricate; apex, rounded. Shape, lower lip: Three-lobed, imbricate; apex, rounded. Margin, upper and lower lips: Entire. Texture, upper and lower lips: Smooth, glabrous. Texture, throat: Smooth, glabrous. Texture, tube: Slightly pubescent. Color, upper and lower lips: When opening, upper surface: Close to 71C. When opening, lower surface: Close to 72C. Fully opened, upper surface: Close to 71C. Fully opened, lower surface: Close to 71D. Color, nectar guides: Close to 163B. Color, throat: Close to 71C. Color, tube: Close to 71D; longitudinal lines, close to NN155C.

*Calyx*.—Arrangement: Cup-shaped calyx with five fused sepals. Sepal length: About 2 cm. Sepal width: About 1.2 cm. Sepal shape: Ovate. Sepal apex: Acute. Sepal margin: Entire. Color, immature, upper and lower surfaces: Close to 144C. Color, mature, upper and lower surfaces: Close to 144C.

*Peduncles*.—Length: About 4.7 cm. Diameter: About 1.3 mm. Aspect: Semi-upright. Texture: Pubescent. Color: Close to 144C.

*Reproductive organs*.—Stamens: Quantity per flower: Four. Stamen length: About 3.9 cm. Anther shape: Ellipsoidal. Anther size: About 2 mm by 2.8 mm. Anther color: Close to 2D. Pollen amount: Moderate. Pollen color: Close to 2D. Pistils: Quantity per flower: One. Pistil length: About 4 cm. Style color: Close to 145D. Stigma shape: Ellipsoidal. Stigma color: Close to 145D. Ovary color: Close to 142D. Seeds and fruits: Seed and fruit development has not been observed on plants of the new *Asarina*.

Garden performance: Plants of the new *Asarina* have been observed to have good garden performance and to tolerate rain, wind and temperatures ranging from about 5° C. to about 35° C.

Pathogen & pest resistance: Plants of the new *Asarina* have not been observed to be resistant to pests and pathogens common to *Asarina* plants.

It is claimed:

1. A new and distinct *Asarina* plant named 'Sunlorose' as illustrated and described.

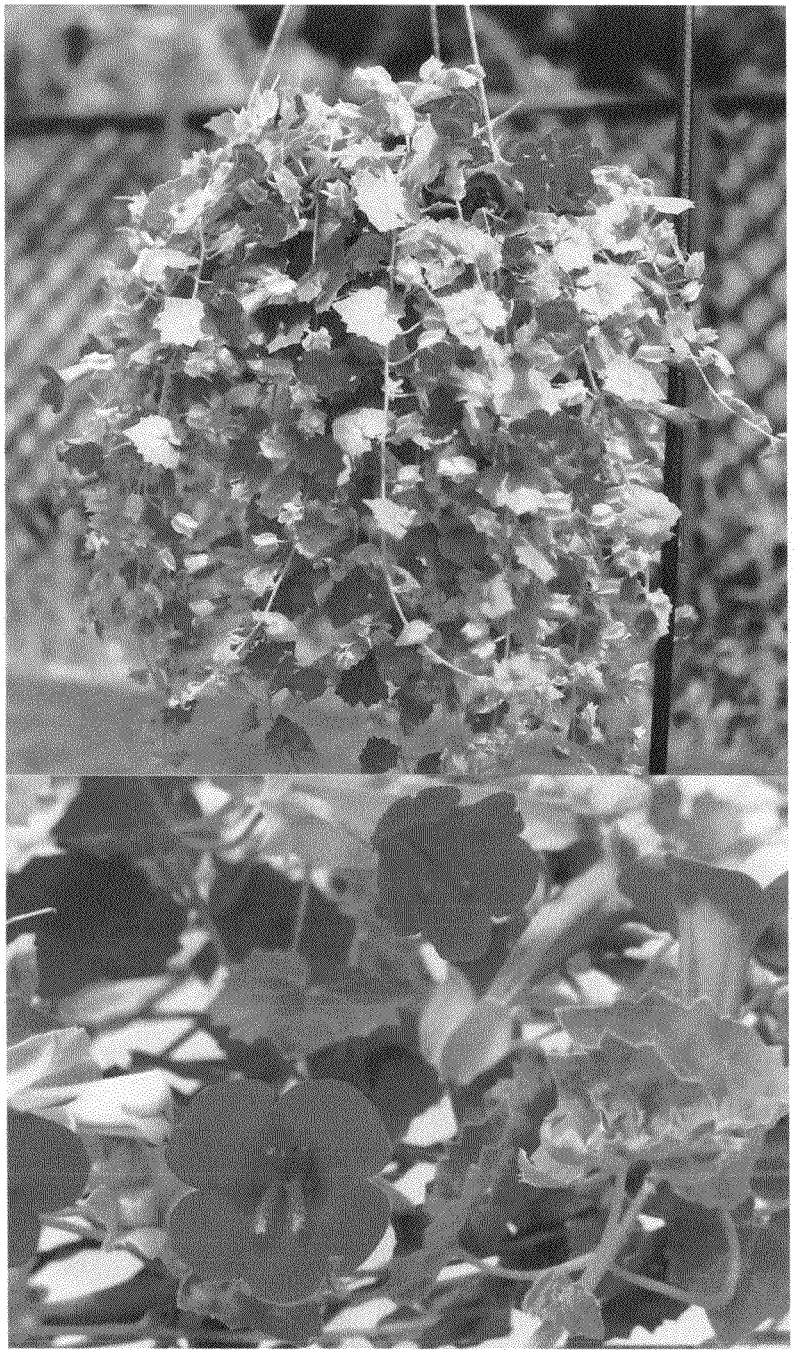

* * * * *